United States Patent
Chavez et al.

(10) Patent No.: US 9,404,908 B2
(45) Date of Patent: Aug. 2, 2016

(54) NON-INVASIVE IMAGING TO THE BLASTOCYST STAGE FOR THE DETECTION OF HUMAN EMBRYONIC ANEUPLOIDY

(71) Applicant: The Board of Trustees of the Leland Stanford Junior University, Palo Alto, CA (US)

(72) Inventors: Shawn L. Chavez, Fremont, CA (US); Brooke Friedman, Stanford, CA (US); Barry Behr, Palo Alto, CA (US); Renee A. Reijo Pera, Los Altos, CA (US)

(73) Assignee: The Board of Truestees of the Leland Stanford Junior University, Stanford, CA (US)

(*) Notice: Subject to any disclaimer, the term of this patent is extended or adjusted under 35 U.S.C. 154(b) by 0 days.

(21) Appl. No.: 14/263,819

(22) Filed: Apr. 28, 2014

(65) Prior Publication Data

US 2014/0349334 A1    Nov. 27, 2014

Related U.S. Application Data

(60) Provisional application No. 61/817,219, filed on Apr. 29, 2013.

(51) Int. Cl.
| | | |
|---|---|---|
| A61B 17/43 | (2006.01) | |
| A01N 1/00 | (2006.01) | |
| G01N 33/483 | (2006.01) | |
| A01N 1/02 | (2006.01) | |

(52) U.S. Cl.
CPC .......... *G01N 33/4833* (2013.01); *A01N 1/0226* (2013.01)

(58) Field of Classification Search
None
See application file for complete search history.

(56) References Cited

U.S. PATENT DOCUMENTS

| | | | |
|---|---|---|---|
| 7,963,906 B2 * | 6/2011 | Wong et al. | 600/33 |
| 8,323,177 B2 * | 12/2012 | Wong et al. | 600/34 |
| 8,337,387 B2 * | 12/2012 | Wong et al. | 600/33 |
| 8,721,521 B2 * | 5/2014 | Wong et al. | 600/33 |
| 8,951,184 B2 * | 2/2015 | Wong et al. | 600/33 |
| 2010/0167286 A1 | 7/2010 | Pera et al. | |
| 2011/0092762 A1 | 4/2011 | Wong et al. | |
| 2011/0105834 A1 | 5/2011 | Wong et al. | |
| 2012/0094326 A1 | 4/2012 | Wong et al. | |
| 2012/0095287 A1 | 4/2012 | Wong et al. | |
| 2012/0220030 A1 | 8/2012 | Pera et al. | |
| 2012/0231451 A1 | 9/2012 | Kee et al. | |
| 2013/0162795 A1 | 6/2013 | Wong et al. | |
| 2013/0165745 A1 | 6/2013 | Wong et al. | |
| 2013/0184518 A1 | 7/2013 | Zarnescu et al. | |
| 2013/0225431 A1 | 8/2013 | Chavez et al. | |
| 2014/0087376 A1 * | 3/2014 | Chavez et al. | 435/6.11 |

OTHER PUBLICATIONS

Chavez; et al., "Dynamic blastomere behaviour reflects human embryo ploidy by the four-cell stage." Nat. Commun. (2012), 3:1251.
Chen; et al., "Biomarkers identified with time-lapse imaging: discovery, validation, and practical application." Fertil. Steril. (Mar. 2013), 99(4):1035-43.
Chung; et al., "Theranostic effect of serial manganese-enhanced magnetic resonance imaging of human embryonic stem derived teratoma", Magn. Reson. Med. (Aug. 2012), 66(2):595-9.
Pera; et al., "Non-invasive imaging of human embryos to predict developmental competence.", Placenta. (Sep. 2011), 32 (Suppl 3):S264-7.
Wong; et al., "Non-invasive imaging of human embryos before embryonic genome activation predicts development to the blastocyst stage.", Nat. Biotechnol. (Oct. 2010), 28(10):1115-21.

\* cited by examiner

*Primary Examiner* — Janice Li
(74) *Attorney, Agent, or Firm* — Pamela J. Sherwood; Bozicevic, Field & Francis LLP

(57) ABSTRACT

Methods are provided for the non-invasive imaging of embryos to determine whether they are euploid or aneuploid.

10 Claims, 11 Drawing Sheets

C

D

A

Poor morphology blastocyst

B

Good morphology blastocyst

A

B

NON-INVASIVE IMAGING TO THE BLASTOCYST STAGE FOR THE DETECTION OF HUMAN EMBRYONIC ANEUPLOIDY

BACKGROUND OF THE INVENTION

Infertility is a common health problem that affects 10-15% of couples of reproductive-age. According to the most recently released data, over 175,000 cycles of in vitro fertilization (IVF) were performed in 2012 in the United States alone (cdc.gov/art). This resulted in the culture of more than a million embryos annually with variable, and often ill-defined, potential for implantation and development to term. The live birth rate, per cycle, following IVF was just 29%, while on average 30% of live births resulted in multiple gestations (cdc.gov/art). Multiple gestations have well-documented adverse outcomes for both the mother and fetuses, such as miscarriage, pre-term birth, and low birth rate. Potential causes for failure of IVF are diverse; however, since the introduction of IVF in 1978, one of the major challenges has been to identify the embryos that are most suitable for transfer and most likely to result in term pregnancy.

Previous studies have demonstrated that more than half of human embryos are aneuploid, carrying an abnormal chromosome number, which contributes to the low efficiency of in vitro fertilization (IVF). Traditional methods of evaluating IVF embryos involve subjective assessment of static morphologic criteria. Although there is a relationship between static embryo morphology and ploidy, the correlation has been weak. Consequently, multiple embryos with variable implantation potential may be transferred, leading to both high rates of embryonic loss and increased frequency of multiple gestations with higher and well-documented maternal and perinatal risks.

In an effort to improve IVF success, clinics are increasingly using preimplantation genetic screening (PGS) in combination with growth to blastocyst stage to assist in selection of euploid embryos for transfer. Though invasive, the use of trophectoderm (TE) biopsy and 24-chromosome screening at the Day 5 blastocyst stage is associated with increased success in IVF. Other studies have failed to demonstrate a similar benefit with earlier Day 3 cleavage stage biopsy and fluorescent in-situ hybridization (FISH) assays of limited chromosome number and Day 3 biopsy with 24-chromosome screening is less common. PGS, however, involves additional patient cost, requires that the embryo be removed from its stable culture conditions to be subjected to invasive biopsy and remains illegal in certain countries.

Recent advances with non-invasive imaging have provided a non-invasive means to evaluate embryo viability, and to date reports indicate improved pregnancy rates in IVF clinics compared to standard morphologic embryo evaluation. Potential advantages of incorporating non-invasive imaging to the repertoire of tools available for embryo assessment include earlier embryo selection, thus diminishing the possible risks associated with prolonged culture, as well as avoiding the need for invasive embryo biopsy.

Previously, we and our collaborators used time-lapse imaging to demonstrate that human development to the blastocyst stage can be predicted by measuring cell cycle parameter timing prior to embryonic genome activation (EGA) by Day 2 of development. The parameters included the duration of the first cytokinesis, time between the two-cell and three-cell stage, and time between the three-cell and four-cell stage. We also recently demonstrated that precise cell cycle parameter timing windows are observed in euploid embryos to the four-cell stage, while four-cell aneuploid embryos exhibit diverse cell cycle parameter timing (20). However, whether these or other imaging parameters could be used to assess ploidy at later stages of embryonic development was uncertain.

Prior IVF methods of human embryo evaluation are thus lacking in several respects and can be improved by the present methods, which involve novel applications of time-lapse so microscopy, image analysis, and correlation of the imaging parameters with molecular profiles and chromosomal composition.

BRIEF SUMMARY OF THE INVENTION

Aneuploidy in human embryos is common, with rates as high as 50-80%, contributing to the low efficiency of in vitro fertilization and high incidence of miscarriage. The present invention utilizes non-invasive time-lapse imaging of human embryos from the zygote to the blastocyst stage to determine the ploidy of an embryo. A subset of these parameters are also highly predictive of blastocyst quality and thus assist in embryo selection. These findings show that human embryo development is characterized by precise timing in developmental windows; and aneuploid embryos have altered timing that suggest perturbation of key cell cycle processes.

Compositions and methods are provided for non-invasive imaging evaluation of the ploidy of an embryo in vitro. In the methods of the invention, an embryo is imaged for imaging parameters, including one or more of: (P1) duration of the first cytokinesis; (P2) time between 2nd and 3rd cell (or first and second mitosis); (P3) time between 3rd and 4th cell (or second and third mitosis); (P4) time between 4th and 5th cell; (P5) time between 5th cell and compaction; (P6) time between 5th cell and cavitation.

In some embodiments, a model for determining the ploidy of an embryo utilizes one or more of: (P3) time between 3rd and 4th cell (or second and third mitosis); (P4) time between 4th and 5th cell; (P5) time between 5th cell and compaction; (P6) time between 5th cell and cavitation. In some embodiments, the model utilizes two, three or four of these parameters, e.g. utilizing P6, P5 and P4. Aneuploid embryos typically show a lengthened time for (P3) between second and third mitosis; (P5) time to compaction; and (P6) time to cavitation, while having a decreased (P4) time between the $4^{th}$ and $5^{th}$ cell, relative to a euploid embryo. Time to cavitation (P6) differs most significantly between euploid and aneuploid blastocysts. The severity of the aneuploidy also impacted parameter timing, as high mosaic aneuploid blastocysts deviated more widely in each of the later cell cycle parameters.

In addition to being an indication of ploidy, these imaging parameters are indicative of good blastocyst morphology. Good morphology may refer to known criteria as defined herein, e.g. using quality scores for expansion and hatching, inner cell mass quality and trophectoderm quality. The imaging parameters most highly indicative of good blastocyst morphology are: (P2) time between 2nd and 3rd cell (or first and second mitosis); (P3) time between 3rd and 4th cell (or second and third mitosis); (P5) time between 5th cell and compaction; and (P6) time between 5th cell and cavitation.

Evaluation of embryos that will have a good morphology and that are euploid allows selection of healthy embryos for implantation. Such methods improve IVF procedures by allowing for early transfer of fewer, high quality embryos. These parameters can be used to select the optimal embryos for transfer, cryo-preservation, or PGS analysis during an IVF procedure. These parameters can also be used to distinguish between different qualities of blastocyst, allowing for a ranking of the relative developmental potentials of embryos within a group.

To create a predictive model of blastocyst euploidy, a classification tree may be constructed utilizing selected early (P1, P2, P3) and late parameters (P4, P5, P6). The highest performing model included three parameters: time to cavitation (P6), time to compaction (P5), and time between the three-cell and four-cell stage (P3). Based upon this classification tree, if P5 is <28.6 h and P6 occurs <66.4 h; or if P6 occurs <66.4 h and P3 is <0.96 h, the blastocyst is predicted to be euploid with a specificity of 94%, sensitivity of 71%, PPV of 96%, and NPV 60%.

In one aspect, immature human oocytes are obtained from hormone-stimulated patients and matured in vitro with ovarian paracrine/autocrine factors. In other aspects, dormant follicles may be recruited from the ovary and programmed in vitro to produce oocytes with normal chromosome composition, epigenetic status, RNA expression, and morphology. The oocytes may be derived from other sources as well, such as pluripotent stem cells differentiated in vitro into germ cells and matured into human oocytes. The developmental potential of the oocytes is determined by imaging the maturation process and changes in morphology. The developmental potential of the resulting fertilized embryo is determined by measuring, for example, the parameters or set of parameters described above. Blastocysts predicted to be euploid by the methods of the invention may be selected for further use, e.g. implantation, transfer, cryo-preservation, or PGS analysis.

DETAILED DESCRIPTION OF THE PREFERRED EMBODIMENT

Figure 1:
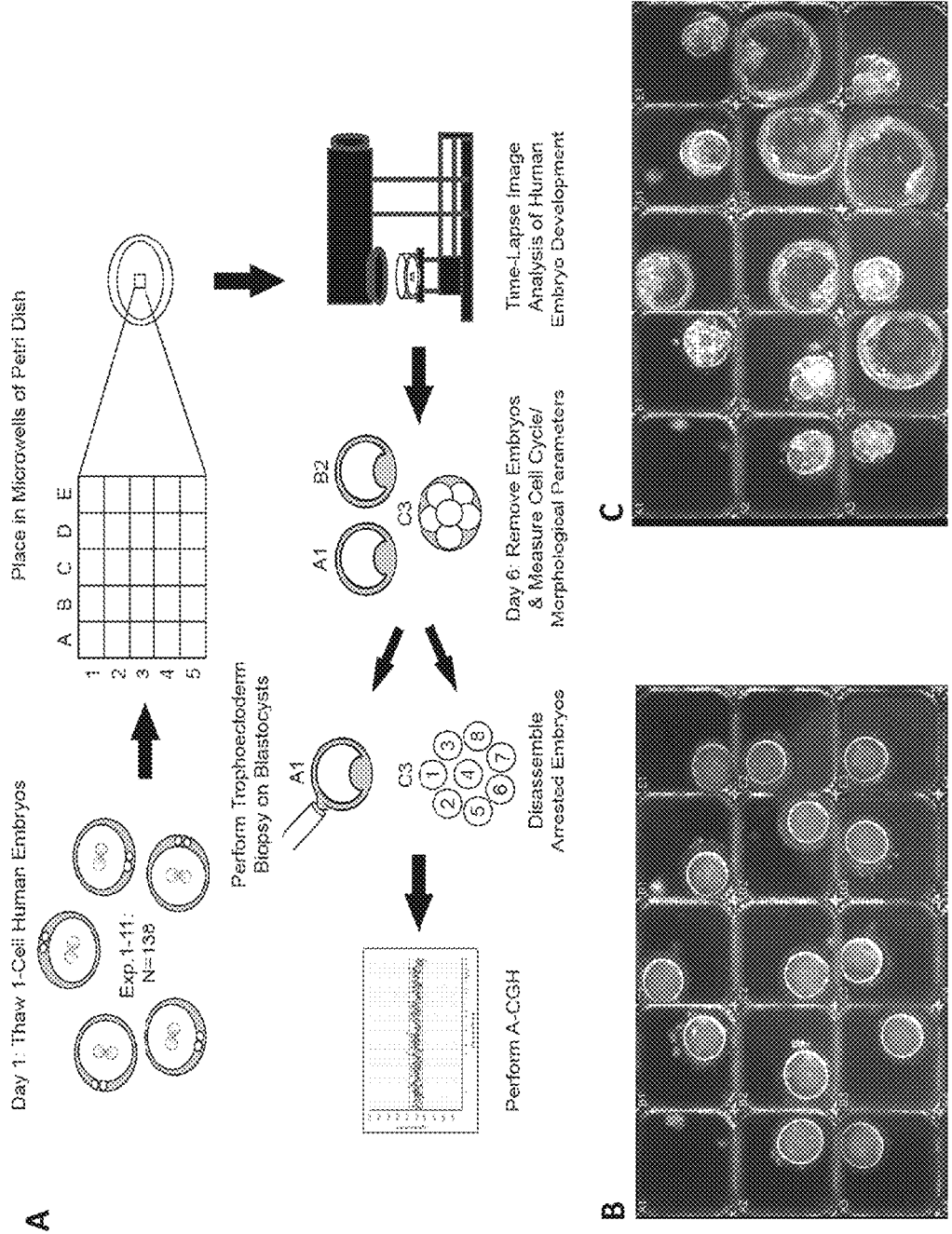
FIG. 1. (A) Experimental design utilizing time-lapse imaging of human embryos. We thawed supernumerary embryos that had been cryopreserved at the zygote stage. Darkfield images were acquired every 5 min up to 6 days (144 h) and compiled into a time-lapse movie for the purpose of cell cycle parameter analysis. Embryos reaching the blastocyst stage underwent trophectoderm biopsy and those that arrested were disaggregated into individual cells. All samples were sent for A-CGH. Individual frames taken from a time-lapse imaging movie on the first day (B) and the sixth day (C) of imaging.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Growing embryos, typically between 1 to 30 per dish, are followed individually by time-lapse imaging with a computer controlled microscope equipped for digital image storage and analysis. Time-lapse imaging can be performed with either inverted microscopes equipped with heated stages and incubation chambers, or custom built miniature microscope arrays that fit inside a conventional incubator. The array of miniature microscopes enables the concurrent culture of multiple dishes of samples in the same incubator, and is scalable to accommodate multiple channels with no limitations on the minimum time interval between successive image capture.

Using multiple microscopes eliminates the need to move the sample, which improves the system accuracy and overall system reliability. The imaging systems use darkfield illumination, although other types of illumination can be used, such as phase contrast, Hoffman modulation contrast, differential interference contrast, or fluorescence. Darkfield illumination provides enhanced image contrast for subsequent feature extraction and image analysis. In addition, near-infrared light sources can be used to reduce phototoxicity and improve the contrast ratio between cell membranes and the inner portion of the cells. The individual microscopes in the incubator can be partially or fully isolated, providing each culture dish with its own controlled environment. This allows dishes to be transferred to and from the imaging stations without disturbing the environment of the other samples.

The embryos can be placed in a standard culture dish, or alternatively in a custom culture dish with optical quality micro-wells. The micro-wells can help prevent undesired motion during culture as well as during dish transport. For a single dish, each micro-well can hold a single embryo, and the entire group of micro-wells shares the same media drop. The bottom surface of each micro-well has an optical quality finish such that the entire group of embryos within a single dish can be imaged simultaneously by a single miniature microscope with sufficient resolution to follow the cell mitosis processes. The culture dish design can also include an outer wall positioned around the micro-wells for stabilizing a media drop, as well as fiducial markers placed near the micro-wells. The hydrophobicity of the surface can be adjusted with plasma etching or another treatment to prevent bubbles from forming in the micro-wells when filled with media.

Analysis of parameters relevant to morphological changes and/or euploidy include at least one of: (P1) duration of the first cytokinesis; (P2) time between 2nd and 3rd cell (or first and second mitosis); (P3) time between 3rd and 4th cell (or second and third mitosis); (P4) time between 4th and 5th cell; (P5) time between 5th cell and compaction; (P6) time between 5th cell and cavitation. Of particular interest are P3, P4, P5 and P6 for analysis of blastocyst ploidy; and P2, P3, P5 and P6 for morphology. In some embodiments, a predictive model is based on P3, P5 and P6.

With respect to early imaging parameters of euploid or good morphology embryos, the first cytokinesis (P1) usually occurs one day after fertilization and has a duration of from about 0 to 33 minutes, where a reference value may be about 0.25 hrs. (P2), the time between first and second cell division is usually between about 1.7 to about 12.7 hours, and for the purpose of the present invention a reference P2 can be considered to be less than about 11 hours. (P3), the time between second and third cell division is usually between about 0.25 to about 1.5 hours, and for the purposes of the present invention a reference P3 can be considered to be less than about 1 hour or less than about 0.96 hours.

With respect to late parameters of euploid or good morphology embryos, (P4) time between 4th and 5th cell has a duration of from about 12 to about 17 hours, and for the purposes of the present invention a reference P4 can be considered to be about 15 hours. P5, time between 5th cell and compaction, has a duration of from about 25 to about 35 hours, and for the purposes of the present invention a reference P5 can be considered to be less than about 29 hours, or less than about 28.6 h. P6, time between 5th cell and cavitation, has a duration of from about 44 to 54 hours, and for the purposes of the invention a reference P6 can be considered to be less than about 66.4 hours.

The imaging step will be over a period of time lasting approximately 48 hours and up to 144 hours (Day 6) or more (plus or minus several hours) after fertilization for purposes of determining embryo quality.

Embryos can be removed from the culture and imaging system and collected as either single embryos or single cells (blastomeres) for gene expression analysis, depending on their state in culture at the time of collection. Each plate typically contains a mixture of normal and abnormal embryos—the embryos that reached the expected developmental stage at the time of harvest are considered normal, whereas those that arrested at earlier developmental stages or fragmented extensively are labelled as abnormal. Gene expression analysis can be performed with high throughput real-time quantitative PCR. Other methods of gene expression analysis may be used, such as microarrays.

To create a predictive model of blastocyst euploidy, a classification tree may be constructed utilizing selected early (P1, P2, P3) and late parameters (P4, P5, P6). The highest performing model included three parameters: time to cavitation (P6), time to compaction (P5), and time between the three-cell and four-cell stage (P3). Based upon this classification tree, if P5 is <28.6 h and P6 occurs <66.4 h; or if P6 occurs <66.4 h and P3 is <0.96 h, the blastocyst is predicted to be euploid with a specificity of 94%, sensitivity of 71%, PPV of 96%, and NPV 60%. Finally an embryo is evaluated based on the imaging analysis. This analysis allows an embryologist to determine the most viable embryo(s) for transfer, cryopreservation, implantation, etc. and to avoid transferring embryos that are not viable. The embryos have not been treated or harmed during the process in any way to hinder successful development after transfer. Further, the present methods may permit earlier transfer of embryos, as well as transfer of fewer embryos in order to increase pregnancy rate and reduce the chance of multiple pregnancies.

Dynamic morphological parameters predictive of embryo viability. The present method comprises image extraction and analysis, preferably from time-lapse image sequences, of different parameters associated with each individual embryo being cultured, including, for example, cell size, thickness of the zona pellucida, degree of fragmentation, symmetry of daughter cells resulting from a cell division, time intervals between the first few mitoses, and duration of cytokinesis.

Images are acquired and stored either on a continuous basis, as in live video, or on an intermittent basis, as in time lapse photography, where a subject is repeatedly imaged in a still picture. Preferably, the time interval between images should be between 1 to 30 minutes in order to capture the significant morphological events as described below. The images shown in the figures were taken at 1 second exposure time every 5 minutes for up to 5 or 6 days. In an alternative embodiment, the time interval between images could be varied depending on the amount of cell activity. For example, during active periods images could be taken as often as every few seconds or every minute, while during inactive periods images could be taken every 10 or 15 minutes or longer. Real-time image analysis on the captured images could be used to detect when and how to vary the time intervals. In our methods, the total amount of light received by the samples is estimated to be equivalent to approximately 24 minutes of continuous low-level light exposure, similar to the total flux received by an average embryo at an IVF clinic during handling. However, the exposure time can be significantly shortened to reduce the total amount of light exposure to the embryos.

"Longer" means longer than normal, which may be determined using routine experimentation by observing a number of embryos or similar cells under the specific conditions used.

This analysis indicates that embryos that follow strict timing in mitosis and cytokinesis are much more likely to be euploid and form a high-quality blastocyst with an expanded inner cell mass (ICM). The dynamic morphological parameters can be used to select the optimal embryos for transfer or cryo-preservation during an IVF procedure. These parameters can also be used to distinguish between different qualities of blastocyst, allowing for a ranking of the relative developmental potentials of embryos within a group. The standard practice in IVF clinics is to transfer at days 3-5. Some clinics choose to culture embryos to the blastocyst stage (day-5), since blastocyst transfer has up to double the implantation rates compared to day-3 transfer. However, many clinics avoid prolonged culture due to potential risk of epigenetic disorders. The predictive imaging parameters can be used to predict embryo viability. This can allow for the transfer or cryo-preservation of embryos earlier than is typically practiced and before the embryos undergo significant changes in their molecular programs. This can also allow for the most optimal embryos to be selected for PGS or other types of analysis such as pre-implantation genetic diagnosis (PGD) of specific disease(s).

The dynamic morphological parameters can be measured manually or measured automatically by image analysis software. Automated feature extraction can eliminate errors due to manual measurement, greatly reduce the time involved in measuring cellular events, and can provide a convenient quantification of the critical parameters necessary for prediction of viability and quality that fits into the normal IVF sample work flow. The image analysis algorithms can employ a probabilistic model estimation technique based on sequential Monte Carlo methods. This technique works by generating distributions of hypothesized embryo models, simulating images based on a simple optical model, and comparing these simulations to the observed image data. Cells are modeled as either collections of ellipses in 2D space or collections of ellipsoids in 3D space (although other appropriate shapes could be used). To deal with occlusions and depth ambiguities, the method can enforce geometrical constraints that correspond to expected physical behavior. To improve robustness, images can be captured at one or more focal planes. The algorithm can be used to automatically measure dynamic morphological parameters such as the duration of cytokinesis and time between mitosis events and make an automated prediction of blastocyst formation and quality.

The analysis can be implemented in a system, e.g. including imaging and data analysis. In some embodiments a computer system programmed or otherwise configured for implementing the methods of the disclosure, such as inputting imaging parameters, classification tree, providing an output of the results, etc. The system includes a central processing unit (CPU, also "processor" and "computer processor" herein), which can be a single core or multi core processor, or a plurality of processors for parallel processing. The system also includes memory (e.g., random-access memory, read-only memory, flash memory), electronic storage unit (e.g., hard disk), communications interface (e.g., network adapter) for communicating with one or more other systems, and peripheral devices, such as cache, other memory, data storage and/or electronic display adapters. The memory, storage unit, interface and peripheral devices are in communication with the CPU through a communications bus (solid lines), such as a motherboard. The storage unit can be a data storage unit (or data repository) for storing data. The system may be operatively coupled to a computer network ("network") with the aid of the communications interface.

The system is in communication with a processing system. The processing system can be configured to implement the methods disclosed herein. In some examples, the processing system is an imaging system, e.g. a camera. The processing system can be in communication with the system imaging through a network, or by direct (e.g., wired, wireless) connection. The processing system can be configured for analysis, such as a classification analysis described herein.

Methods as described herein can be implemented by way of machine (or computer processor) executable code (or software) stored on an electronic storage location of the system, such as, for example, on the memory or electronic storage unit. During use, the code can be executed by the processor. In some examples, the code can be retrieved from the storage unit and stored on the memory for ready access by the processor. In some situations, the electronic storage unit can be precluded, and machine-executable instructions are stored on memory.

The computer-implemented system may comprise (a) a digital processing device comprising an operating system configured to perform executable instructions and a memory device; and (b) a computer program including instructions executable by the digital processing device to create a recurrence index, the computer program comprising (i) a first software module configured to receive data pertaining to imaging parameters; (ii) a second software module configured to relate the imaging parameters and; and (iii) provide an evaluation of blastocyst fitness.

In order to increase pregnancy rates, clinicians often transfer multiple embryos into patients, potentially resulting in multiple pregnancies that pose health risks to both the mother and fetuses. In order to determine the optimal number of embryos to transfer, which is specific to each patient, the embryo viability assessment can be combined with other parameters related to patient characteristics (age), IVF cycle characteristics (fertilization rate), and embryo cohort parameters (total number of embryos), for example. A comprehensive analysis that includes an accurate prediction of embryo viability, combined with patient-specific parameters, can potentially maximize pregnancy rates while reducing the risk of multiples.

The developmental potential of in vitro-matured oocytes can be assessed using time-lapse image analysis during the maturation process as well as during subsequent fertilization and embryo development. For example, the developmental potential of the oocyte can be determined by using time-lapse imaging to measure changes in morphology of the oocyte and its membrane, cytoplasm, nucleus, polar body, and cumulus cells. In addition, the timing of nuclear maturation including germinal vesicle breakdown (GVBD) and the completion of meiotic maturation may be used to assess viability. The imaging data can be correlated with gene expression and genetic/epigenetic profiles of the oocytes before and after maturation to validate the imaging parameters. Once mature, the oocytes can be fertilized to create embryos. The viability of the embryos can be determined by measuring at least one of the imaging parameters described herein.

Experimental

Here we sought to evaluate whether previously established parameter timing could distinguish euploid from aneuploid embryos beyond the four-cell stage and whether additional cell cycle parameters up to the blastocyst stage correlate with embryonic ploidy status. We analyzed a unique cohort of embryos that had been cryopreserved at the one-cell stage prior to assessment of quality and thus, were representative of the spectrum of embryos obtained in the IVF setting. This is in contrast to embryos typically consented for research, which are generally suboptimal, as they have been triaged for discard following developmental failure or poor morphology.

Utilizing frozen-thawed embryos is a reliable proxy for fresh embryo development as frozen-thawed embryos have been shown to have comparable, if not improved implantation and pregnancy rates, as compared to fresh embryos, and studies utilizing time-lapse imaging of fresh embryos suggest that the cryopreservation process does not delay developmental kinetics.

Experimental design for evaluating parameters and embryonic ploidy. To evaluate the utility of non-invasive imaging for the detection of aneuploidy at the blastocyst stage, we thawed 138 supernumerary embryos that had been cryopreserved at the zygote stage, previously donated to research by couples who had undergone IVF (FIG. 1A). Darkfield images of embryo development were acquired every 5 min up to 6 days (approximately 144 hours) (FIGS. 1B,C) and compiled into a time-lapse movie for the purpose of cell cycle parameter analysis by three independent reviewers. From a series of 11 experiments, 115 of 138 zygotes were retrieved post-thaw, 106 progressed beyond the one-cell stage and 57 reached the blastocyst stage, for a blastocyst formation rate of 53.8%. Nine embryos were excluded for technical reasons such as cell lysis or loss.

TABLE 1A

Early parameters and embryonic ploidy (including blastocysts and arrested embryos).

| | Aneuploid Embryos (n = 41) | Euploid Embryos (n = 37) | P-value |
|---|---|---|---|
| Normal Parameters | 10/36 (27.8%) | 26/36 (72.2%) | P < 0.001 |
| Abnormal Parameters | 31/42 (73.8%) | 11*/42 (26.2%) | |

*6 of 11 with daughter cell dividing from 1 to 3 cells

TABLE 1B

Early parameters and blastocyst ploidy.

| | Aneuploid blastocysts (n = 16) | Euploid blastocysts (n = 35) | P-value |
|---|---|---|---|
| Normal parameters | 7/33 (21.2%) | 26/33 (78.8%) | P = 0.057 |
| Abnormal parameters | 9/18 (50%) | 9*/18 (50%) | |

*6/9 with daughter cell dividing 1:3 cells

On Day 6, embryos that had reached the blastocyst stage underwent trophectoderm (TE) biopsy, and the TE cells were analyzed by 24-chromosome array-comparative genomic hybridization (A-CGH). Embryos that had arrested prior to reaching the blastocyst stage were manually disaggregated and individual blastomeres were analyzed by single cell ACGH (FIG. 1A). Embryos were considered aneuploid if one or more cells contained an abnormal chromosome number. Initially, polar body biopsy was also performed in an effort to further interrogate embryo chromosomal composition. However, given the high incidence of post-zygotic chromosomal events and the potential negative impact of polar body biopsy on embryo quality and blastocyst development, we chose to perform only TE biopsy in subsequent experiments as we deemed it the most reliable method of assessing embryo ploidy.

We obtained 27 arrested embryos and 51 blastocysts with information regarding chromosomal status. Nineteen arrested embryos were excluded because of DNA amplification failure, which explains the number of arrested embryos as compared to blastocysts with A-CGH results and is likely due DNA degradation in the arrested embryos.

Figure 7:
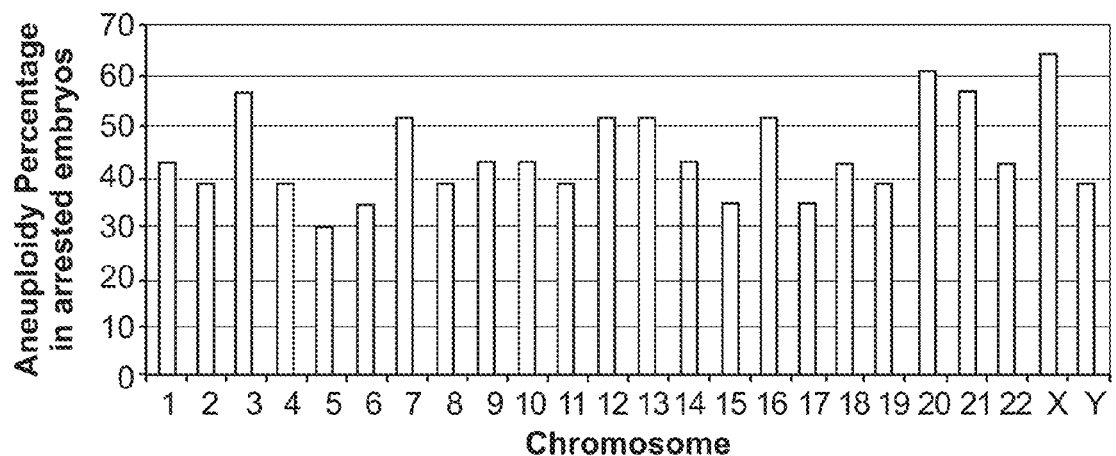
FIG. 7A-B. (A) Chromosomal analysis of arrested embryos. Abnormalities in both arrested embryos and blastocysts affected all autosomes and sex chromosomes and did not preferentially segregate to particular chromosomes. Arrested embryos tended to be high mosaic, whereas blastocysts tended to be low mosaic aneuploid. (B) Consistent with previous studies, the early parameters (P1, P2, P3) were highly predictive of blastocyst formation.
Figure 7:
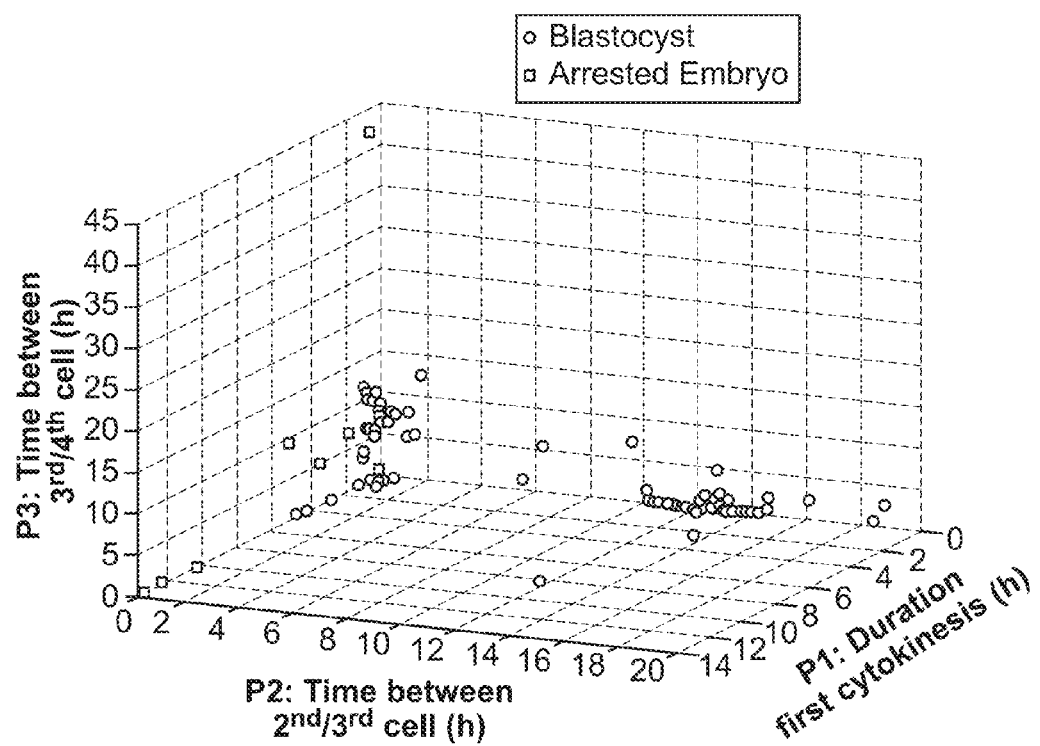

Prediction of blastocyst development with early cell cycle parameters. Consistent with our previous work, three cell cycle parameters measured by Day 2 were highly predictive of blastocyst development: duration of the first cytokinesis (P1), time between the two-cell and three-cell stage (P2), and time between the three-cell and four-cell stage (P3) (FIG. 7B). Embryos were considered to have normal early cell cycle parameters if each of these three parameters fell into optimal timing windows as previously established by our group: P1 (0-33 min), P2 (7.8-14.3 h), P3 (0-5.8 h). If one or more cell cycle parameters fell out of these optimal time ranges, the embryo was considered to have abnormal early parameters.

In accordance with previous findings, 90.2% of embryos with normal early cell cycle parameters, developed into blastocysts (p<0.001) (Table 2). The majority of embryos with abnormal early parameters underwent arrest (69.2%), yielding a sensitivity of 81.6%, specificity of 35.1%, positive predictive value of 97.6%, and a negative predictive value of 30.8% with Fisher's exact test.

TABLE 2A

Early and late parameters and blastocyst ploidy Results expressed as medians (range).

| Parameters | Aneuploid blastocysts (n = 16) | Euploid blastocysts (n = 35) | P-value |
|---|---|---|---|
| P1: First cytokinesis duration (h) | 0.25 (0.2-2.5) | 0.25 (0.2-9.1) | NS |
| P2: Time between $2^{nd}/3^{rd}$ cell (h) | 9.92 (0-16) | 11.2 (0.08-14.6) | NS |
| P3: Time between $3^{rd}/4^{th}$ cell (h) | 3.96 (0-17.1) | 0.83 (0-26.4) | 0.007 |
| P4: Time between $4^{th}/5^{th}$ cell (h) | 10.6 (0-19.3) | 14.8 (3-45.8) | 0.02 |
| P5: Time to compaction (h) | 44.8 (28.7-70.4) | 32.7 (17.6-69.1) | 0.001 |
| P6: Time to cavitation (h) | 67.7 (40.9-94.3) | 48.7 (35.7-80.2) | 0.0004 |

TABLE 2B

Early and late parameters and blastocyst morphology Results expressed as medians (range).

| Parameters | Poor morphology blastocysts (n = 22) | Good morphology blastocysts (n = 29) | P-value |
|---|---|---|---|
| P1: First cytokinesis duration (h) | 0.25 (0.2-4.2) | 0.25 (0.2-9.1) | NS |
| P2: Time between $2^{nd}/3^{rd}$ cell (h) | 1.2 (0-16) | 11.7 (0.3-14.6) | <0.001 |
| P3: Time between $3^{rd}/4^{th}$ cell (h) | 4.0 (0.25-26.4) | 0.67 (0-4.7) | <0.001 |
| P4: Time between $4^{th}/5^{th}$ cell (h) | 13.5 (0-45.8) | 14.3 (3-27) | NS |
| P5: Time to compaction (h) | 43.3 (24.3-70.4) | 32.6 (17.6-59.8) | 0.0002 |
| P6: Time to cavitation (h) | 63.2 (40.9-94.3) | 48.3 (35.7-79.3) | 0.0003 |

Aneuploidy rates in arrested embryos and blastocysts. Of the 27 arrested embryos, 25 were aneuploid (92.6%). The two arrested embryos with a euploid result only had one blastomere amplify, raising the question of whether these embryos were truly euploid, or perhaps, that the other blastomeres which failed to amplify were aneuploid. These findings are in line with previous work demonstrating that chromosomally abnormal embryos are more likely to undergo developmental arrest. In contrast, only sixteen out of 51 blastocysts were aneuploid, for a blastocyst aneuploidy rate of 31.4%. Consistent with our previous work, we determined that the aneuploidies observed in arrested embryos were not more commonly associated with a certain subset of chromosomes, but rather all 22 pairs of autosomes and both sex chromosomes were affected (FIG. 7A). Indeed, the aneuploidies detected in the blastomeres of arrested embryos were quite complex, in contrast to the aneuploidies observed in the blastocysts, which tended to be predominantly simple trisomies and monosomies (Table 3).

TABLE 3

Early Parameters and blastocyst Development

| | Arrested embryos (n = 49) | Blastocysts (n = 57) | P-value |
|---|---|---|---|
| Normal early parameters | 4/41 (9.8%) | 37/41 (90.2%) | P < 0.001 |
| Abnormal early parameters | 45/65 (69.2%) | 20*/65 (30.8%) | |

*7 blastocysts with daughter cell dividing from 1 to 3 cells

Based on previous findings, we classified embryos with defects in more than four chromosomes as "high mosaic" and those with errors in four chromosomes or less as "low mosaic." Chromosomes were considered affected if there was either a whole chromosome or sub-chromosomal error. To clarify, our use of the term "mosaic" does not refer to variations between blastomeres, but rather to errors in multiple chromosomes within a given blastomere or TE biopsy. While aneuploid blastocysts were predominately low mosaic, the majority of aneuploid arrested embryos were high mosaic.

Figure 2:
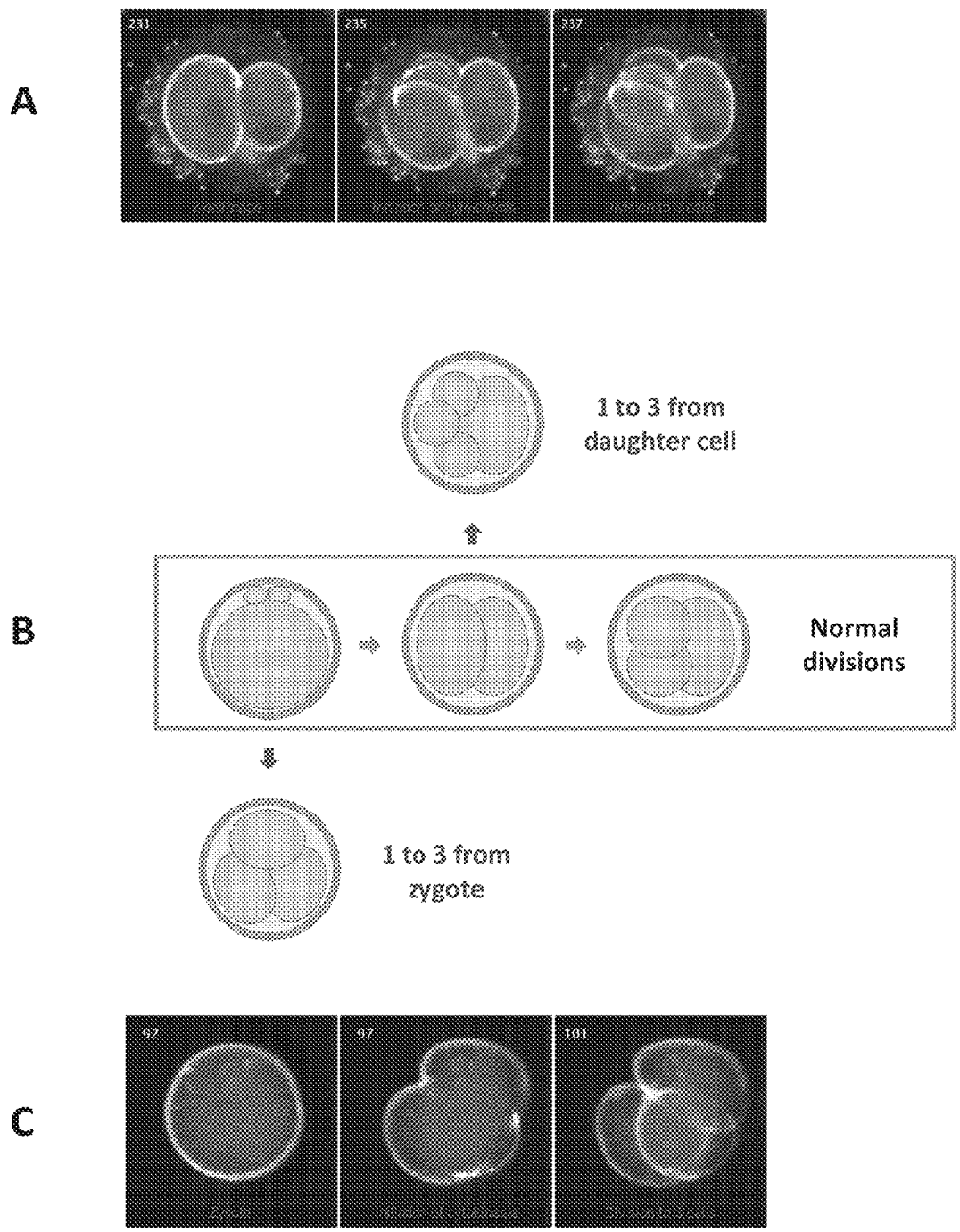
FIG. 2. Daughter cell division from one to three cells. (A) Time-lapse imaging depicts daughter cell division from one to three cells. (B) In this schematic representation, note the difference between one to three cell division of the daughter cell, as compared to direct zygote division from the one to three cell stage, also shown in time-lapse imaging (C).

Unique pattern of daughter cell division from one to three cells. In embryos that developed to the blastocyst stage, we observed a common and unique pattern of division, not previously described, of one or more daughter cells dividing from one cell to three cells at the two-cell stage. This pattern of daughter cell division from one to three cells (FIG. 2A) is distinct from the pattern of division in which the 1-cell zygote divides directly to three blastomeres (FIG. 2C). The latter pattern of division direct from one-cell zygote to three cells is often associated with triploidy and decreased implantation rates. Of the 20 embryos with abnormal early parameters that developed into blastocysts, seven of these embryos exhibited this daughter cell division from one to three cells (Table 4). Moreover, this unique pattern of daughter cell division was frequent among euploid blastocysts with abnormal parameters suggesting this may represent a form of embryo adaptation that ultimately allows for maintenance of the proper number of chromosomes.

TABLE 4

Blastocyst Aneuploidies

| | Aneuploidy | Morphologic Grade | Early Parameters |
|---|---|---|---|
| 1 | Trisomy 22, monosomy 21 | 6CA | Normal |
| 2 | Monosomy 8.10, trisomy 19 | EB1 | Normal |
| 3 | Duplication of q arm of 7 (7q33-7q36.3) | 6AA | Normal |

TABLE 4-continued

Blastocyst Aneuploidies

| | Aneuploidy | Morphologic Grade | Early Parameters |
|---|---|---|---|
| 4* | −1, −5, −6, −9, −17, −20 | EB2 | Normal |
| 5 | Trisomy 12, monosomy 11 | 4AB | Normal |
| 6 | Monosomy 6 | EB1 | Normal |
| 7* | +1, −2, −4, +5, −7, +8, −9, −10, +11, +12, +13, +14, +15, +17, −18, +19, +20 −21, −22.00 | 3CC | Abnormal |
| 8 | Monosomy 10 | 4CC | Abnormal |
| 9* | Deletion 1, monosomy of 8, 13, 18, 19 | EB1 | Abnormal |
| 10 | Monosomy 7 | EB2 | Abnormal |
| 11 | Monosomy 21 | EB1 | Abnormal |
| 12 | Monosomy 3, 10, 17 | EB1 | Abnormal |
| 13 | Monosomy 21 | EB2 | Abnormal |
| 14* | Deletion 14, −2, −4, −7, −9, −16, −17, XYY | EB1 | Abnormal |
| 15 | Monosomy 17, 19 | EB2 | Abnormal |
| 16 | Trisomy 16 | 4BC | Abnormal |

*High mosaic aneuploid blastocyst with >4 chromosome affected

Early cell cycle parameters are predictive of embryonic ploidy. We next sought to evaluate the relationship between early cell cycle parameter timing and ploidy. Normal early cell cycle parameters (P1, P2, P3) were found to be strongly predictive of embryonic ploidy, when including both arrested embryos and blastocysts. Of those embryos with normal early parameters, 72.2% were euploid and of those with abnormal early parameters, 73.8% were aneuploid (p<0.0001) (Table 1A). When focusing specifically on normal early parameters among blastocysts, there was a trend (78.8%) towards normal early parameters and blastocyst euploidy, although this was not statistically significant (p=0.057) (Table 1B).

Of embryos with abnormal early parameters, 50% were euploid and 50% were aneuploid. This analysis may be limited by the smaller number of aneuploid blastocysts in this cohort; of the nine euploid blastocysts with abnormal parameters, six exhibited the pattern previously described of daughter cell division from one to three cells. In addition, when comparing the medians of the early parameters, we found that euploid blastocysts exhibited a significantly shorter time between the appearance of the third and fourth cells (Table 2A). Differences in the other early parameters of P1 and P2 did not vary significantly between euploid and aneuploid blastocysts.

Figure 3:
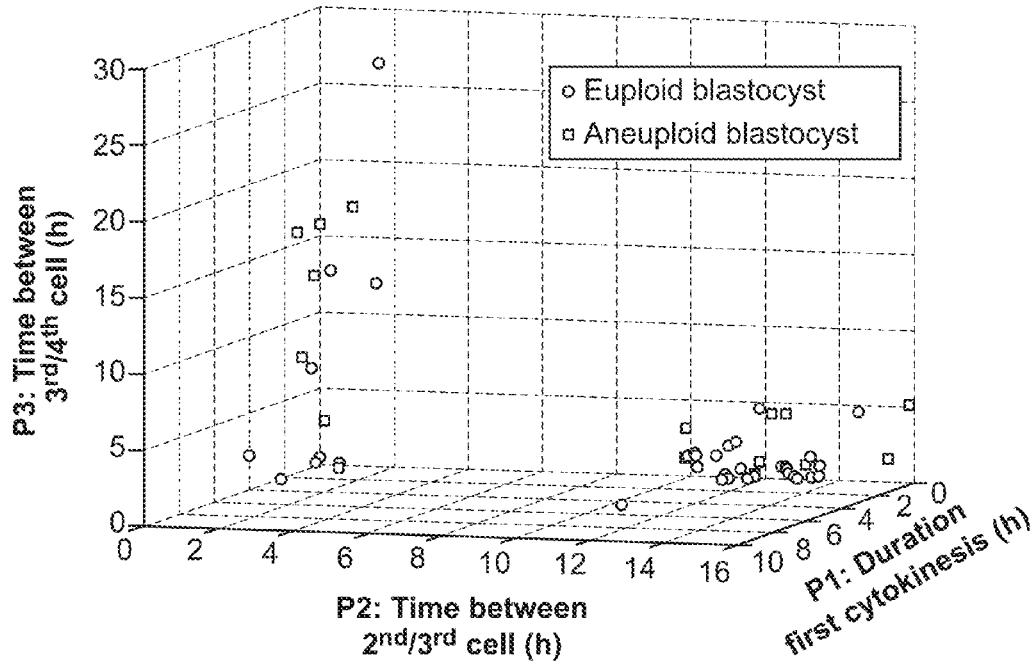
FIG. 3. Association between early cell cycle parameters and blastocyst ploidy. (A) Euploid blastocysts (red circles) tended to cluster in an optimal time range window. Although there was some overlap with aneuploid blastocysts (blue squares), aneuploid blastocysts tended to segregate in a different location. (B) The majority of euploid blastocysts that fell outside the optimal time range windows exhibited daughter cell division from one to three cells (blue circles), a unique pattern of division not previously described. There were only two aneuploid blastocysts with daughter cell division from one to three (black triangles), with one embryo falling into a different embryo cluster. (C) Blastocysts with a high degree of aneuploid mosaicism varied more widely in early parameter timing, as compared to low mosaic blastocysts. Three of the four high mosaic aneuploid blastocysts (black star) fell far outside the early parameter timing windows of the other embryo clusters. Low mosaic aneuploid blastocysts (blue square) overlapped more with the euploid blastocysts (red circle). (D) Abnormalities across all chromosomes were seen in aneuploid blastocysts, with no preferential association to particular chromosomes.
Figure 3:
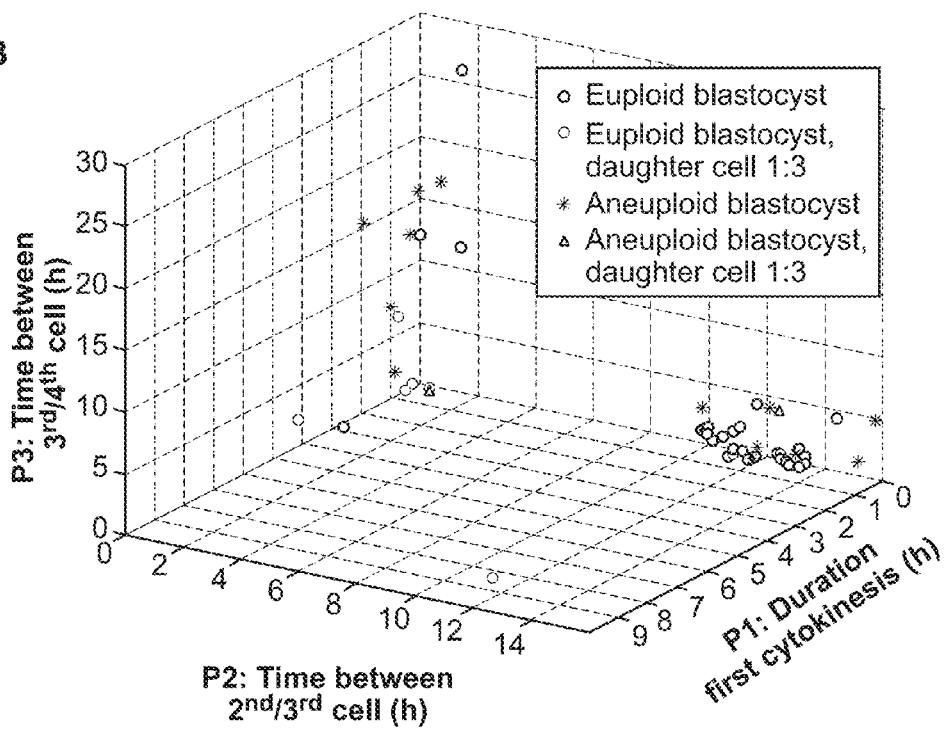
Figure 3:
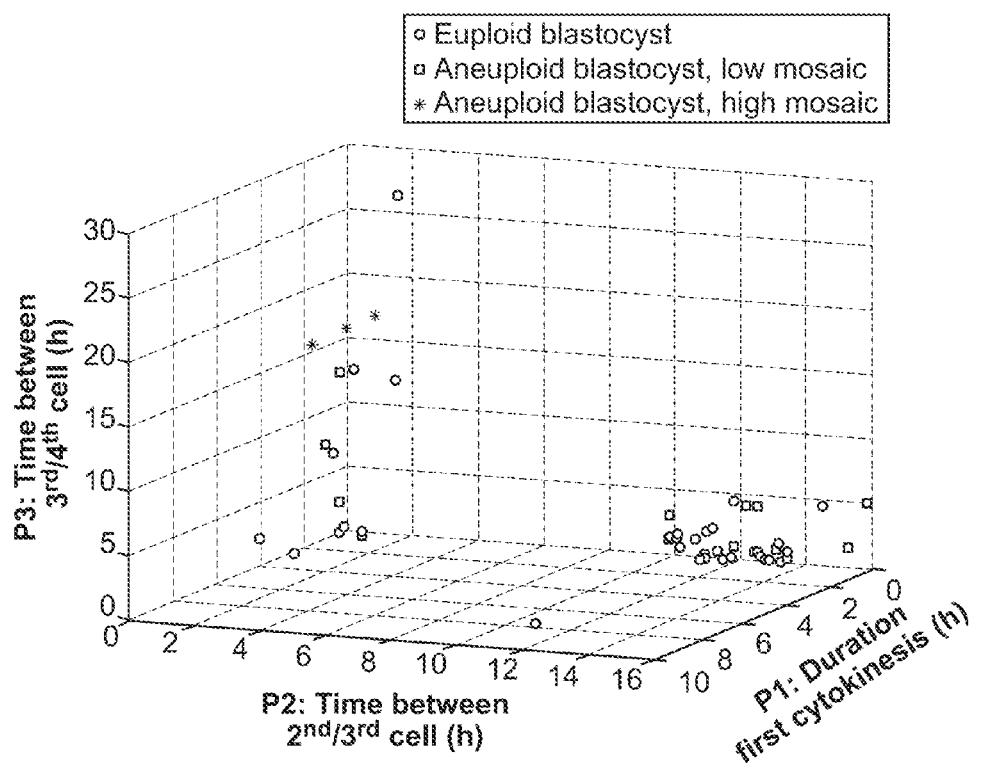
Figure 3:
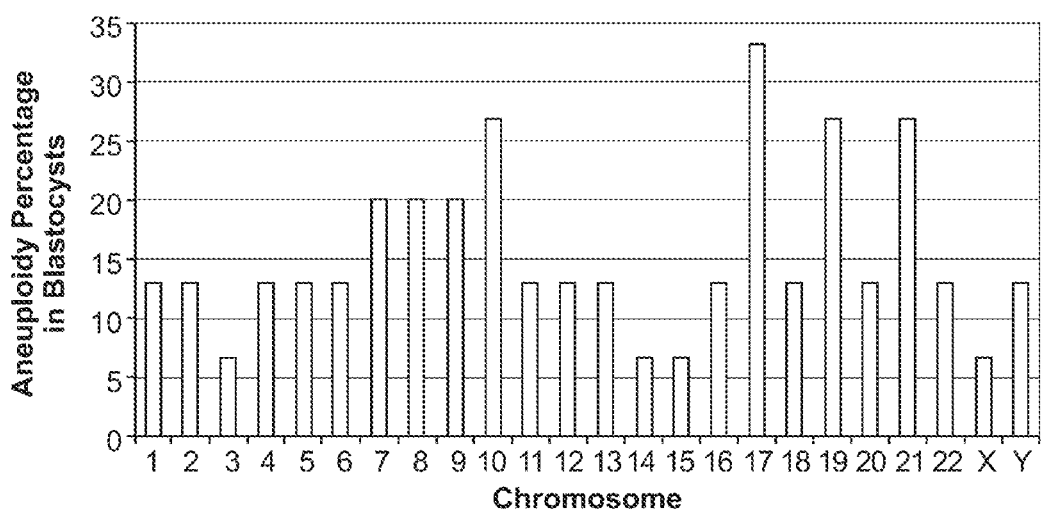

To further analyze the relationship between the early parameters and blastocyst ploidy, we graphed each embryo as a point in a three-dimensional (3D) plot, where each dimension represented a cell cycle parameter (FIG. 3A). Although there was some overlap in parameter timing with aneuploid blastocysts, euploid blastocysts tended to cluster together in a region within the optimal time windows our group has previously described. There was a smaller second clustering of euploid blastocysts that fell outside the optimal time windows, which predominately represented those embryos with daughter cells that divided from one to three cells and resulted in a shorter P2 and longer P3 (FIG. 3B). In addition, aneuploid blastocysts with high mosaicism varied more widely from the cell cycle parameters of euploid blastocysts, than did aneuploid blastocysts with low mosaicism, particularly in time between the three-cell and four-cell stage (FIG. 3C and Table 5).

TABLE 5

Frequency of daughter cell division 1:3 cells among blastocysts

| | Normal parameters euploid blatsocysts | Normal parameters aneuploid blastocysts | Abnormal parameters euploid blastocysts | Abnormal parameters aneuploid blastocysts |
|---|---|---|---|---|
| Daughter Cell Division 1:3 | 3/26 | 1/7 | 6/9 | 1/9 |

Later cell cycle parameters are correlated with blastocyst ploidy. We next examined cell cycle parameters that occurred beyond Day 2: time between four cell and five-cell stage (P4), time from fifth cell appearance to compaction (P5) and time from fifth cell appearance to cavitation (P6). As seen in Table 2A, each of these later parameters differed significantly between euploid and aneuploid blastocysts. Euploid blastocysts demonstrated a significantly longer P4, consistent with previous investigators who found that a short time to appearance of the fifth cell was associated with lower implantation rates. Suggesting that there is a relationship between developmental rate and ploidy, euploid blastocysts progressed faster from the five-cell stage to both compaction and cavitation as compared to aneuploid blastocysts (Table 2A and FIG. 4C).

Figure 4:
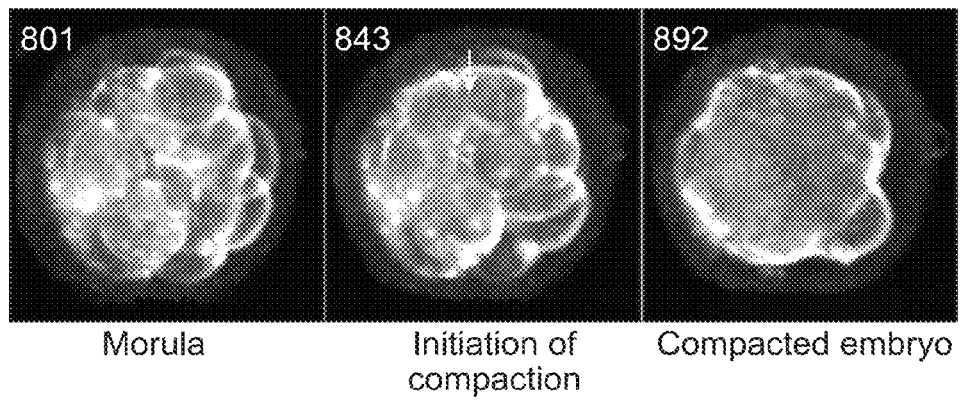
FIG. 4. Correlation between later cell cycle parameters and blastocyst ploidy. (A) Time-lapse images depicts the initiation of compaction, as defined as the first time a cell is seen to lose a portion of its membrane and merge with an adjoining cell. (B) Time-lapse images demonstrate the initiation of cavitation, as the emergence of a blastocele is seen for the first time. (C) Euploid blastocysts (red circles) exhibited a longer time to fifth cell appearance and shorter time to compaction and cavitation, and therefore clustered in a particular location on this 3D plot. Aneuploid blastocysts (blue squares) segregated away from the euploid blastocysts because of their different parameter timing. (D) Similar to the divergence seen in early parameters with high mosaic blastocysts, all four high mosaic blastocysts (black stars) were outside the euploid blastocyst cluster (red circles) when plotting the later cell cycle parameters. Again, there was more overlap of low mosaic aneuploid blastocysts (blue squares) with the euploid blastocysts.
Figure 4:
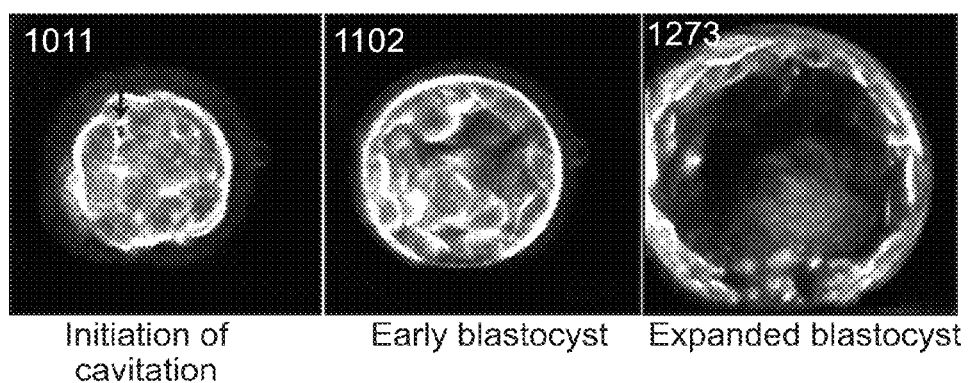
Figure 4:
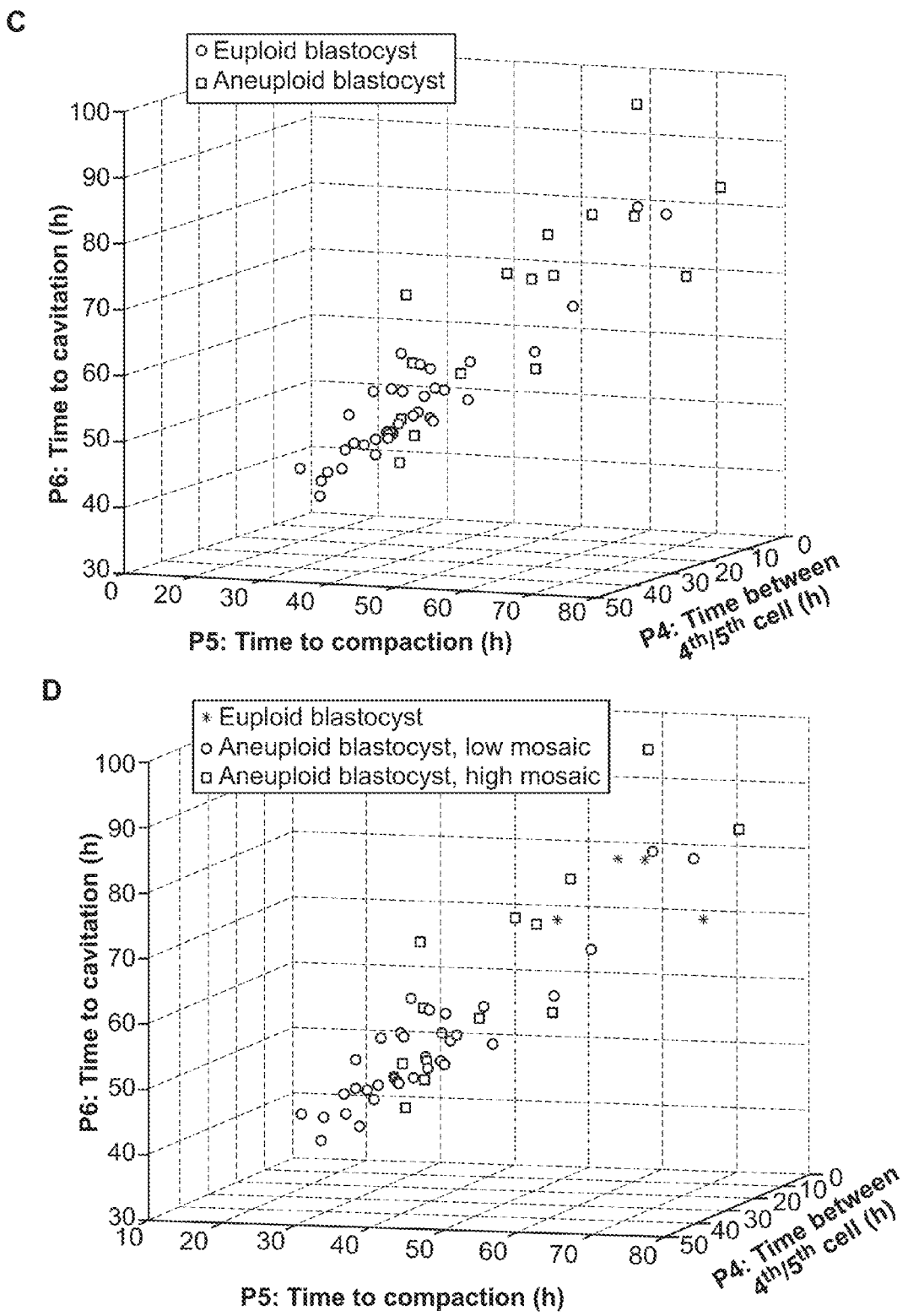

Out of all six early and late parameters, (P6) time to cavitation differed most significantly between euploid and aneuploid blastocysts. The severity of the aneuploidy also impacted parameter timing, as high mosaic aneuploid blastocysts deviated more widely in each of the later cell cycle parameters. (FIG. 4D, Table 6). From euploid, to low mosaic to high mosaic aneuploid blastocysts, P4 became progressively shorter and P5 and P6 grew progressively longer with each category, respectively.

TABLE 6

Impact of aneuploid mosaicism on parameter measurements in blastocysts. Results expressed as median values.

| Parameter | Euploid blastocyst (n = 35) | Low mosaic aneuploid (n = 12) | High mosaic aneuploid (n = 4) | P-value |
|---|---|---|---|---|
| P1: Duration of first cytokinesis | 0.25 | 0.25 | 0.25 | NS |
| P2: Time between $2^{nd}/3^{rd}$ cell (h) | 11.2 | 11.0 | 0.8 | NS |
| P3: Time between $3^{rd}/4^{th}$ cell (h) | 0.83 | 3.4 | 16.0 | 0.02 |
| P4: Time $4^{th}/5^{th}$ cell (h) | 15.0 (8.5-45.8) | 12.0 (0-19.3) | 0.6 (0-14.8) | 0.02 |
| P5: Time to compaction (h) | 32.6 (17.6-69.1) | 42.6 (38.7-70.4) | 58.7 (45.8-66.0) | 0.001 |
| P6: Time to cavitation (h) | 48.7 (35.6-80.2) | 62.3 (40.9-94.2) | 73.0 (67.8-80.3) | 0.006 |

Figure 8:
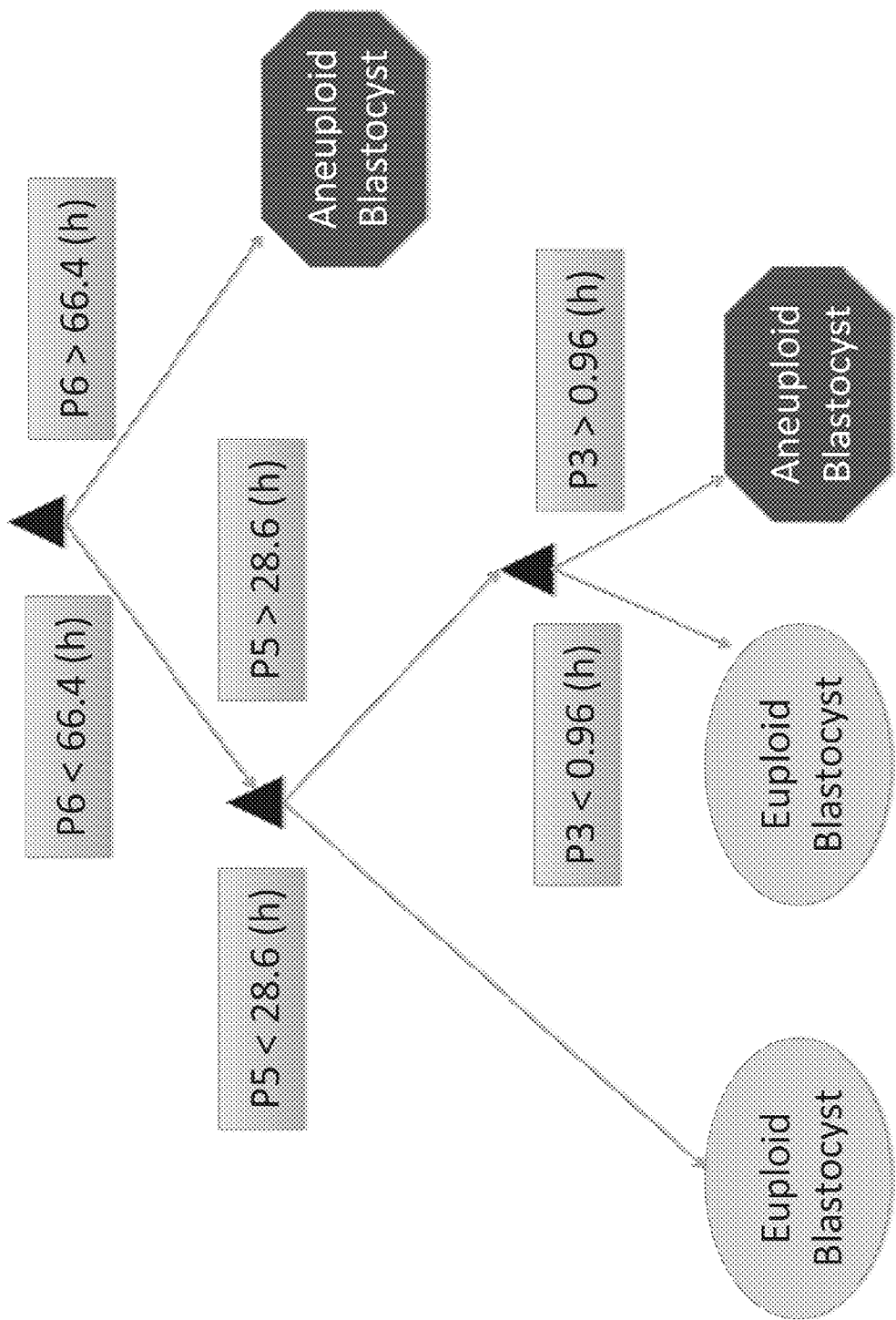
FIG. 8. Based upon this classification tree, if P5 is <28.6 h and P6 occurs <66.4 h; or if P6 occurs <66.4 h and P3 is <0.96 h, the blastocyst is predicted to be euploid with a sensitivity of 71%, specificity of 94%, PPV of 96%, and NPV 60%. This classification tree is consistent with our findings that P3, P5 and P6 varied most significantly between euploid and aneuploid blastocysts.

Model utilizing early and late parameters for blastocyst ploidy prediction. To create a predictive model of blastocyst euploidy, a classification tree was constructed utilizing all the early and late parameters as candidates for the model (FIG. 8). The highest performing model included three parameters: time to cavitation (P6), time to compaction (P5), and time between the three-cell and four-cell stage (P3). Based upon this classification tree, if P5 is <28.6 h and P6 occurs <66.4 h; or if P6 occurs <66.4 h and P3 is <0.96 h, the blastocyst is predicted to be euploid with a specificity of 94%, sensitivity of 71%, PPV of 96%, and NPV 60%. This classification tree is consistent with our findings that P3, P5 and P6 differed most significantly between euploid and aneuploid blastocysts.

Early cell cycle parameters are strongly predictive of blastocyst morphology. As morphologic grading is typically used to guide clinical decisions regarding which embryo(s) to transfer, we analyzed morphology and its relationship to parameter timing and ploidy. Blastocysts were given a numeric score based upon the morphologic grade assigned by an embryologist. We found that blastocysts with poor morphology were more likely to be aneuploid, with 12/22 (57.1%) poor morphology blastocysts exhibiting aneuploidy and only 4/29 (13.8%) good morphology blastocysts with aneuploidy (p=0.003). Complex aneuploidies were particularly associated with poor morphology, as all high mosaic aneuploid blastocysts received the lowest morphologic grades. Conversely, the blastocyst with the highest morphologic grade only exhibited a subchromosomal deletion. This is consistent with previous studies suggesting a relationship between poor morphology and aneuploidy, with more complex aneuploidies being associated with poorer blastocyst morphology and slower development.

Figure 5:
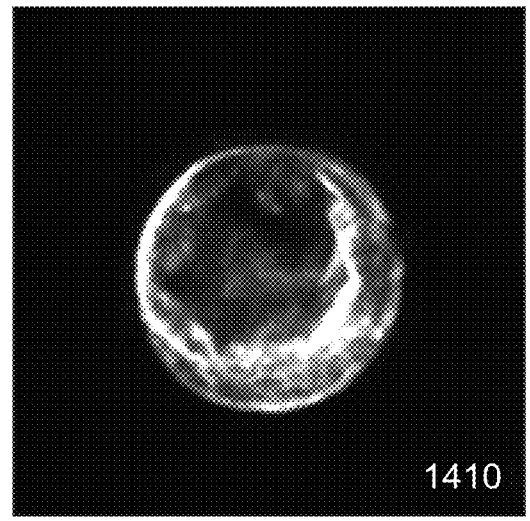
FIG. 5. Cell cycle parameter prediction of blastocyst morphology. (A) Time-lapse image examples of a poor morphology blastocyst and a good morphology blastocyst (B) as evaluated by a clinical embryologist. Note that the ICM of the poor morphology blastocyst is difficult to visualize and the trophectoderm has fewer cells forming a loose epithelium, in contrast to the good morphology blastocyst which has a distinct, tightly packed ICM with many cells and a trophectoderm layer with many cells forming a cohesive epithelium. (C) Early cell cycle parameters in the first two days were strongly predictive of embryo development into good morphology blastocysts (red circles) as opposed to poor morphology blastocysts (blue squares). (D). Similar to timing among euploid blastocysts, good morphology blastocysts exhibited shorter time to compaction and cavitation as compared to poor morphology blastocysts.
Figure 5:
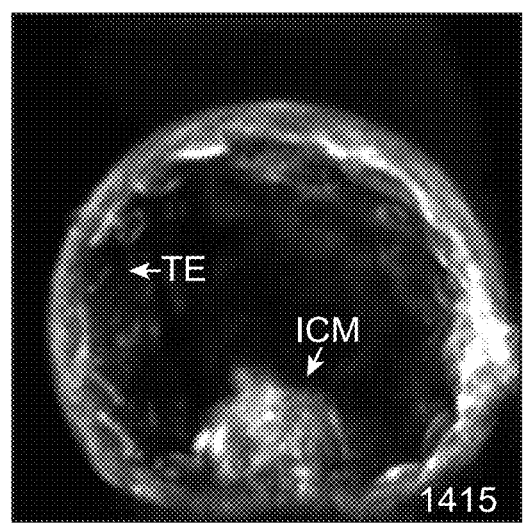
Figure 5:
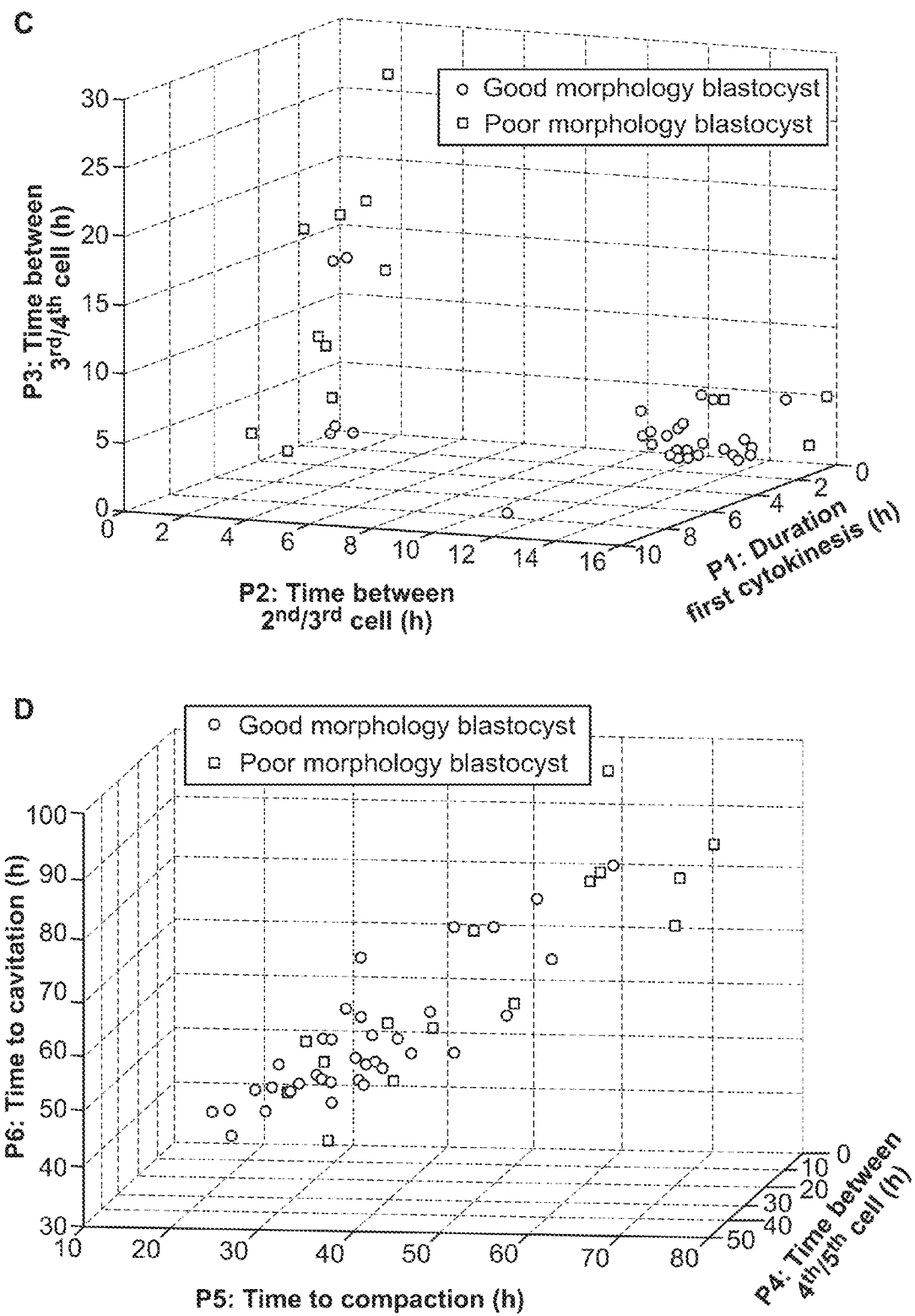
Figure 6:
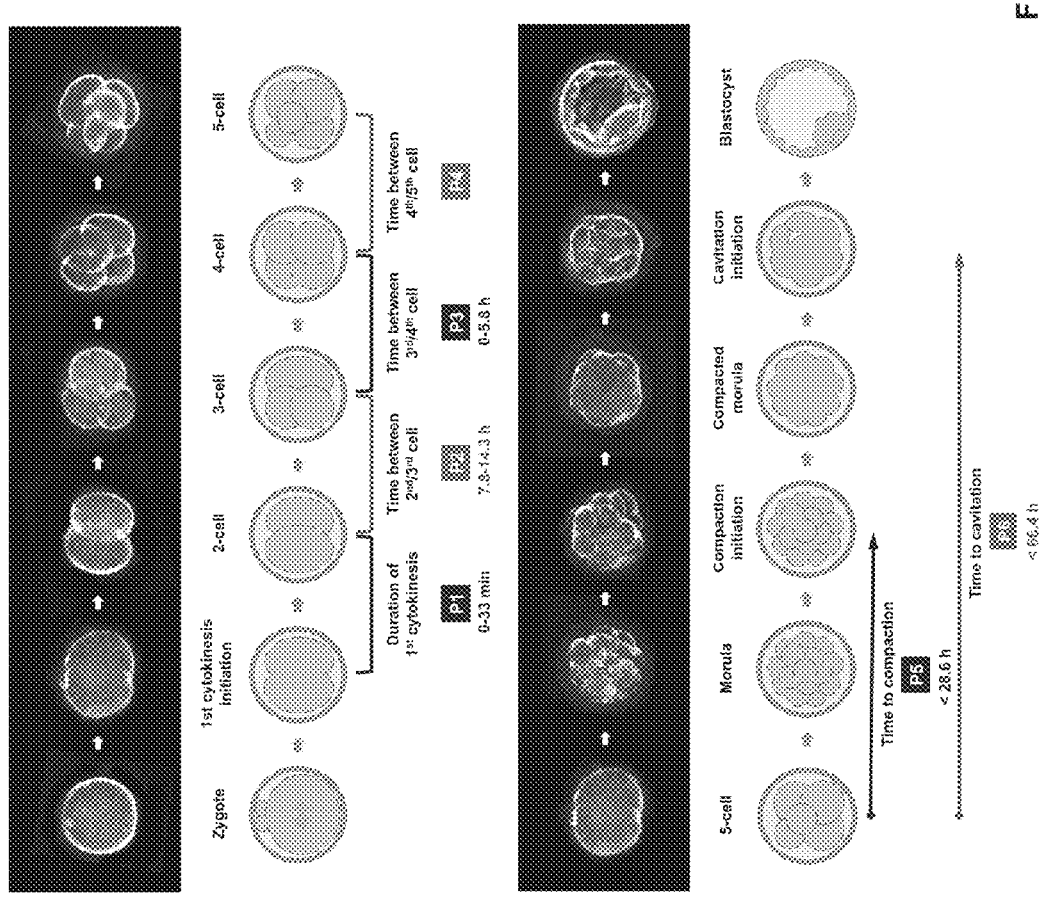
FIG. 6. Summary of cell cycle parameters. The early parameters of cytokinesis duration (P1), time between the two-cell and three-cell stage (P2) and time between the three-cell and four-cell stage (P3) are noted to have optimal time ranges as previously established by our group. For P3, our group previously established the range of 0-5.8 h for the prediction of blastocyst development, but we determined an optimal time of <0.96 h for the prediction of blastocyst euploidy. For the later parameters of time to compaction (P5) and to cavitation (P6), the optimal windows for prediction of blastocyst euploidy were determined to be <28.6 h and <66.4 h respectively. Time between the four-cell and five-cell stage (P4) did not appear to be a robust predictor of blastocyst ploidy and we were not able to determine an optimal time range for this parameter.

We next investigated how both early and late parameters correlate with blastocyst morphology and found that normal early parameters were strongly predictive of good blastocyst morphology. Approximately 76% of embryos with normal early parameters formed good morphology blastocysts while 72.2% of embryos with abnormal early parameters formed poor morphology blastocysts (p=0.001) (Table 7). In addition, P2 and P3 differed significantly between poor and good morphology blastocysts (Table 2B). This is in line with previous studies that demonstrated that synchronicity in appearance between the third and fourth cells is associated with improved blastocyst morphology. Plotting these early cell cycle parameters in a 3D plot, good morphology blastocysts clustered tightly together and poor morphology blastocysts tended to segregate away from optimal timing windows (FIGS. 5C,D).

TABLE 7

Early parameters and blastocyst morphology

| | Poor morphology blastocysts (n = 22) | Good morphology blastocysts (n = 29) | P-value |
|---|---|---|---|
| Normal early parameters | 8/33 (24.2%) | 25/33 (75.8%) | P = <0.001 |
| Abnormal early parameters | 14/18 (77.8%) | 4/18 (22.2%) | |

Although P4 varied significantly between aneuploid and euploid blastocysts, there did not appear to be a significant difference between poor and good morphology blastocysts in this parameter. Similar to euploid blastocysts, good morphology blastocysts underwent compaction and cavitation at significantly earlier times than poor morphology blastocysts (Table 2B and FIG. 5D). Thus, it appears that cell cycle parameter timing prior to Day 2 is not only highly predictive of blastocyst formation, but also predictive of which embryos will develop into good morphology blastocysts, which are most likely to be selected for embryo transfer.

Here, we demonstrate that previously-identified early cell cycle parameters are highly predictive of embryonic ploidy beyond the four-cell stage and that additional novel parameters later in development assist in the determination of which embryos are more likely to form euploid blastocysts. These data catalog significant differences throughout pre-implantation development in both early and late imaging parameters in euploid versus aneuploid embryos to the blastocyst stage. Moreover, this is the largest study to date to perform comprehensive chromosomal analysis of individual blastomeres from human embryos that arrest prior to the blastocyst stage.

It is noted that embryos with complex aneuploidies continue to divide and are typically able to survive up to Day 3, a stage at which programmed cell death is first initiated in the human embryo secondary to embryonic genome activation. Consequently, A-CGH studies have found lower aneuploidy rates among blastocysts as compared to cleavage stage embryos, which is likely due to aneuploid embryo arrest beginning on Day 3. This is consistent with our findings that, with only two exceptions, arrested embryos were overwhelmingly aneuploid. The nearly uniformly aneuploid constitution of arrested embryos has important clinical implications as clinicians can counsel patients to forego transfer of embryos that are likely to harbor chromosomal errors and result in a failed IVF cycle or miscarriage.

As the average maternal age of our embryo cohort was low and paternal meiotic errors are suggested to be nominal, the high prevalence of monosomies among aneuploid blastocysts suggests that chromosome loss during mitosis is a common mechanism that occurs in aneuploid embryos that reach the blastocyst stage. Our work contradicts previous data suggesting that most monosomies are unable to form blastocysts, and supports more recent studies demonstrating that any chromosome(s) can be affected in embryo and it may still form a blastocyst.

We found that euploid blastocysts tended to cluster together within specific optimal time ranges for early cell cycle parameter and that aneuploid, particularly high mosaic aneuploid blastocysts, varied widely. This correlates with our previous work that euploid embryos at the four-cell stage tended to cluster tightly together, whereas aneuploid embryos were divergent in different ways from optimal timing windows. Among the three early parameters described, the time between appearance of the third and fourth cells differed most between aneuploid and euploid blastocysts. This is line with clinical data demonstrating quicker division from the three-cell to four-cell stage in embryos that successfully implanted after transfer. Although there was a statistically significant difference in time between the four-cell and five-cell stage among euploid versus aneuploid blastocysts, it was not as robust a predictor as P3, P5 and P6.

We chose to analyze parameters as independently as possible in order to avoid "umbrella" parameters with multiple measures within one parameter that may mask important variations in cell cycle timing between embryos. Few studies have examined the timing of embryo parameters beyond the appearance of the fifth cell, and controversy exists regarding the importance of blastocyst development rate on ploidy status. We report a shorter time from the five-cell stage to compaction and to cavitation is associated with euploid status in blastocysts. We observed a stronger correlation between timing of compaction and cavitation and euploidy than other investigators, perhaps because they utilized "umbrella" parameters and acquired images only every 20 min, as opposed to every 5 min in our study. We also observed in this study that both early and late imaging parameters were strongly predictive not only of which embryos would ultimately form blastocysts, but also of which embryos would form good morphology blastocysts. Interestingly, the ability of an embryo to develop into a good morphology blastocyst appears to be linked to division kinetics within the first two days of development, which may impact the timing windows of later imaging parameters. Although studies have suggested a relationship between good morphology of blastocysts and IVF success morphologic evaluation is limited, in that embryo development is dynamic and a single assessment can miss subtle variations in division kinetics that are unique to each embryo. Clinical studies can be used to validate the relationship between morphology, cell cycle parameters, and blastocyst ploidy, as the findings presented allow embryo selection without subjecting embryos to invasive biopsy.

Materials and Methods

Sample source and procurement two pronuclear supernumerary human embryos from previous IVF cycles, subsequently donated for molecular research, were obtained with written informed consent from the Stanford University RENEW Biobank. Embryos in the RENEW Biobank are received from several IVF clinics across the country. De-identification was performed according to the Stanford University Institutional Review Board-approved protocol #10466 entitled 'The RENEW Biobank' and the molecular analysis of the embryos was in compliance with institutional regulations. No protected health information was associated with individual embryos. Embryos originated from 20 patients, 7 of whom utilized donor oocytes. Average maternal age was 31.6 years of age. If the age of the oocyte donor was unknown, age was assumed to be 25 years for the purpose of overall average age calculation.

Human embryo thawing and culture Human embryos that had been cryopreserved at the two-pronuclei stage were thawed by a two-step rapid thawing protocol using Quinn's Advantage Thaw Kit (CooperSurgical, Trumbull, Conn.) as previously described (19). Either cryostraws or vials were removed from the liquid nitrogen and exposed to air before incubating in a 37° C. water bath. Once thawed, embryos were initially transferred to a 0.5 mol/L sucrose solution, then to a 0.2 mol/L sucrose solution each for 10 mins. The embryos were then transferred to a microdrop of Global media (Life Global Group, Guilford, Conn.) supplemented with 10% Life Global protein supplement (Life Global Group, Guilford, Conn.). Embryos were cultured under mineral oil (Sigma, St Louis, Mo.) at 37° C. with 6% CO2, 5% O2 and 89% N2, standard human embryo culture conditions in accordance with current clinical IVF practice. Embryos were cultured in custom polystyrene petri dishes with individual microwells located in the center to track embryo identity during imaging and subsequent handling. Each microwell accommodates one embryo. Group culture of embryos is maintained through the common media drop shared by the microwells. Small markers (letters and numbers) are located near the microwells for embryo identification. Of note, the culture media was not replenished on Day 3 as is recommended by manufacturer guidelines, given concern for interruption of time lapse imaging and risk of embryo loss. This did not appear to negatively impact embryo development as high blastocyst development rates were achieved.

Time-lapse imaging Embryos were monitored continuously using a microscope system inside a conventional incubator. The system consists of an inverted digital microscope with light-emitting diode illumination, ×10 Olympus objective, manual focus knob and 5-megapixel CMOS camera. The microscope was modified for darkfield illumination by placing a darkfield aperture between the collimated white light-emitting diode and the condenser lens as previously described (19). Images were taken at a 0.6 s exposure time every 5 min up to 6 days (144 h).

Parameter measurement and analysis After each experiment, images were compiled into a time-lapse movie with well identification labels and timestamps that allowed manual measurement of the imaging parameters. To guarantee blinded parameter measurements, three independent investigators manually measured the time interval for each parameter before receiving the A-CGH results. Measurement of early cell cycle parameters has been previously described (19). Appearance of the fifth cell was defined as the time between the appearance of a cleavage furrow to produce the fourth cell and the appearance of a cleavage furrow to produce the fifth cell. Time to compaction (P5) and time to cavitation (P6) were both measured from the appearance of the cleavage furrow to produce the fifth cell. Compaction was defined as the first time that one of the cells lost a portion of its membrane and merged with an adjoining cell. Cavitation was defined as the first appearance of a blastocoele cavity.

Embryo morphologic assessment All embryos reaching the blastocyst stage were assigned a morphologic grade by an embryologist on Day 6 according to the Gardner and Schoolcraft method. Blastocysts were given a number based on the degree of expansion and hatching status (from 1 to 6). For blastocysts beyond stage 1 or 2, a second score of "A," "B," or "C" was assigned to the inner cell mass (ICM) and the TE. For the purpose of analysis, a numeric score was calculated for each blastocyst based upon the morphologic grad.

The score for ICM can be graded as (A) many cells tightly packed; (B) several cells loosely grouped and (C) very few cells. The score for trophectoderm quality can be graded as (A) many cells, cohesive layer; (B) few cells, loose epithelium; (C) very few large cells. Three points were given for a grade of "A", two points for "B" and 1 point for C, and these individual numbers were multiplied by the numeric score for degree of expansion and hatching, where (1) blastocoel cavity less than half the colume of the embryo; (2) blastocoel cavity more than half the volume of the embryo; (3) full blastocoel, cavity completely filling the embryo; (4) expanded blastocyst, cavity larger than the embryo with thinning of the shell; (5) hatching out of the shell; (6) hatched out of the shell. Blastocysts receiving a grade of EB1 were given 1 point overall and EB2 received 2 points. Embryos receiving a total numeric score of <8 were considered poor morphologic grade and those with a score of >8 were considered good morphologic grade.

Embryo biopsy and disaggregation In the first two experiments, polar body biopsy was performed on 15 embryos prior to initiation of imaging. All biopsy procedures were performed on the heated stage of an Olympus IX70 microscope (Olympus Australia, Mt. Waverley, Victoria, Australia) equipped with Eppendorf micromanipulators (Eppendorf AG, Hamburg, Germany) using Origio Humagen pipettes (Origio, Malov, Denmark) in dishes prepared with droplets of SAGE modified HTF with 10% SPS (Cooper Surgical, Trumbull, Conn.) under mineral oil. A ZILOS-tk laser (Hamilton Thorne Biosciences, Beverly, Mass.) was used to breach the ZP. The polar body biopsy pipette was used to gently aspirate the polar bodies. Polar bodies were washed once in a separate drop of wash buffer and transferred to 0.2 ml PCR tubes. If two distinct polar bodies were seen, efforts were made to aspirate the polar bodies separately and place them in separate PCR tubes. After embryos were imaged, on Day 6 all embryos were removed from the imaging system. Blastocysts underwent TE biopsy. An estimated three to ten TE cells were drawn into the lumen of a biopsy pipette and pulled gently away from the blastocyst. Detachment of the TE cells was achieved with pulses from the laser. Biopsied TE cells were washed three times in separate drops of wash buffer and then transferred to 0.2-mL PCR tubes. All embryos that arrested prior to the blastocyst stage were transferred to Acidified Tyrode's Solution (Millipore) to remove the ZP. After ZP removal, embryos were disaggregated in Quinn's advantage calcium and magnesium-free medium with Hepes plus 10% human albumin (CooperSurgical). Once disaggregated, each blastomere was washed three times in 10 ml drops of non-stick wash buffer and transferred to a sterile 0.2 mL PCR tube.

Array-comparative genomic hybridization (A-CGH). DNA extraction and preamplification was accomplished using the SurePlex Kit according to the manufacturer's instructions (BlueGnome). In brief, the DNA was extracted from each sample as well as the reference sample, denatured and then preamplified with PicoPlex pre-amp enzyme. Following whole genome amplification, each sample was fluorescently labeled with either Cy3 or Cy5 and hybridized to the BlueGnome CytoChip. Scanned images were analyzed and chromosomal copy number ratios quantified and reported using the CytoChip algorithm and BlueFuse software (Blue-Gnome). Threshold levels and whole chromosomal losses or gains were determined by three times the s.d., 4±0.3 log 2 ratio call, or both as previously described (44).

Statistical analysis The individual parameter data is represented by medians, as most parameters were not normally distributed. Normality of tested distributions was evaluated using D'Agostino-Pearson Omnibus test. The Mann-Whitney U-test was used to determine if the median values between euploid and aneuploid blastocysts were significantly different. Kruskal Wallis was utilized to compare the median parameters of euploid, low mosaic and high mosaic aneuploid blastocysts. Statistical significance (P≤0.05) was determined for proportions using Fisher's Exact Test. CART (Classification And Regression Trees) was used to determine a predictive model of blastocyst euploidy by employing an exhaustive grid search of all possible univariate splits to find the splits for an appropriate classification tree. To avoid overfitting, decision branches were required to be based upon a minimum of 10 data points (i.e. embryos).

What is claimed:

1. A method for selecting a human embryo for transfer or cryopreservation based on an evaluation of quality of embryo growth in vitro, comprising:
    measuring an imaging parameter (P3) of the time between 3rd and 4th cell or second and third mitosis of the test embryo and measuring at least one imaging parameter selected from: (P4) time between 4th and 5th cell; (P5) time between 5th cell and compaction and (P6) time between 5th cell and cavitation;
    comparing the P3 imaging parameter and the at least one imaging parameter from the test embryo to a reference imaging parameter; determining whether the imaging parameters from the test embryo differs from the reference imaging parameters, wherein the P3 reference imaging parameter is less than about 1 hour, the reference P4 is about 15 hours, the reference P5 is less than about 28.6 hours, the reference P6 is less than about 66.4 hours; wherein a difference indicates a lack of embryo quality;
    providing an evaluation of the test embryo quality based on comparison and determination; and
    selecting an embryo for transfer or cryopreservation based on the evaluation of quality.

2. The method of claim 1 wherein embryo quality comprises one or both of morphology and ploidy.

3. The method of claim 2, wherein high quality embryos have one or more of: shortened P5 relative to the reference imaging parameter; shortened P6 relative to the reference imaging parameter, and lengthened P4 relative to a reference imaging parameter.

4. The method of claim 1, wherein the method further comprises measuring an imaging parameter (P3) of the time between 3rd and 4th cell (or second and third mitosis) of the test embryo and wherein imaging parameters P3, P4, P5 and P6 from the test embryo are compared to reference imaging parameters.

5. The method of claim 1, wherein a classification tree is constructed wherein if P5 is <28.6 h and P6 occurs <66.4 h; or if P6 occurs <66.4 h and P3 is <0.96 h, the blastocyst is predicted to be euploid with a specificity of 94%, sensitivity of 71%, PPV of 96%, and NPV 60%.

6. The method of claim 1, where the embryos are human pre-implantation embryos derived from oocytes that have been matured in vitro.

7. The method of claim 1, where the measurements are used to rank a group of embryos based on blastocyst morphology.

8. The method of claim 1, comprising using time-lapse imaging to measure the at least one parameter.

9. The method of claim 1, wherein evaluation of test embryo quality is performed as a series of steps embodied as a program of instructions executable by computer and performed by means of software components loaded into the computer.

10. The method of claim 2, wherein embryo quality comprises ploidy.

* * * * *